United States Patent
Wang et al.

(10) Patent No.: US 8,966,868 B2
(45) Date of Patent: Mar. 3, 2015

(54) METHODS OF STABILIZING MOLECULAR WEIGHT OF POLYMER STENTS AFTER STERILIZATION

(75) Inventors: Yunbing Wang, Sunnyvale, CA (US);
Derek Mortisen, San Francisco, CA (US); Xiao Ma, Santa Clara, CA (US);
Fuh-Wei Tang, Temecula, CA (US);
Byron Lambert, Temecula, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 907 days.

(21) Appl. No.: 13/103,890

(22) Filed: May 9, 2011

(65) Prior Publication Data
US 2012/0285123 A1    Nov. 15, 2012

(51) Int. Cl.
*B65B 63/08*        (2006.01)
*C04B 7/345*        (2006.01)
*C04B 7/34*         (2006.01)

(52) U.S. Cl.
USPC .............................................. 53/432; 53/440

(58) Field of Classification Search
USPC .................................................... 53/432, 440
IPC .. B65B 63/08; F17C 1/00,2209/00; C04B 7/34, C04B 7/345
See application file for complete search history.

(56) References Cited

U.S. PATENT DOCUMENTS

| | | | |
|---|---|---|---|
| 6,996,952 B2 * | 2/2006 | Gupta et al. | 53/434 |
| 7,785,647 B2 * | 8/2010 | Ding | 427/2.1 |
| 7,959,857 B2 * | 6/2011 | Freeman et al. | 422/22 |
| 8,147,769 B1 * | 4/2012 | Huang et al. | 422/243 |
| 8,207,240 B2 * | 6/2012 | Lambert et al. | 522/74 |
| 8,394,446 B2 * | 3/2013 | Ding | 427/2.1 |
| 8,524,151 B2 * | 9/2013 | Freeman et al. | 422/22 |
| 2008/0090934 A1 | 4/2008 | Muratoglu et al. | |
| 2008/0215142 A1 | 9/2008 | Muratoglu et al. | |
| 2011/0139650 A1 * | 6/2011 | Dworak | 206/363 |

OTHER PUBLICATIONS

International Search Report for PCT/US2012/036962 mailed Aug. 30, 2012, 11 pgs.

* cited by examiner

*Primary Examiner* — Christopher Harmon
(74) *Attorney, Agent, or Firm* — Squire Patton Boggs (US) LLP (57) ABSTRACT

Methods of stabilizing the molecular weight of polymer stents scaffolds after E-beam sterilization are disclosed. The molecular weight of the polymer of the irradiated scaffolds is stabilized through exposure to gas containing oxygen.

3 Claims, 7 Drawing Sheets

METHODS OF STABILIZING MOLECULAR WEIGHT OF POLYMER STENTS AFTER STERILIZATION

BACKGROUND OF THE INVENTION

1. Field of the Invention

This invention relates to methods of manufacturing polymeric medical devices, in particular, stents.

2. Description of the State of the Art

This invention relates to radially expandable endoprostheses, that are adapted to be implanted in a bodily lumen. An "endoprosthesis" corresponds to an artificial device that is placed inside the body. A "lumen" refers to a cavity of a tubular organ such as a blood vessel. A stent is an example of such an endoprosthesis. Stents are generally cylindrically shaped devices that function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

Stents are typically composed of scaffolding that includes a pattern or network of interconnecting structural elements or struts, formed from wires, tubes, or sheets of material rolled into a cylindrical shape. This scaffolding gets its name because it physically holds open and, if desired, expands the wall of the passageway. Typically, stents are capable of being compressed or crimped onto a catheter so that they can be delivered to and deployed at a treatment site.

Delivery includes inserting the stent through small lumens using a catheter and transporting it to the treatment site. Deployment includes expanding the stent to a larger diameter once it is at the desired location. Mechanical intervention with stents has reduced the rate of restenosis as compared to balloon angioplasty. Yet, restenosis remains a significant problem. When restenosis does occur in the stented segment, its treatment can be challenging, as clinical options are more limited than for those lesions that were treated solely with a balloon.

Stents are used not only for mechanical intervention but also as vehicles for providing biological therapy. Biological therapy uses medicated stents to locally administer a therapeutic substance. Effective concentrations at the treated site require systemic drug administration which often produces adverse or even toxic side effects. Local delivery is a preferred treatment method because it administers smaller total medication levels than systemic methods, but concentrates the drug at a specific site. Local delivery thus produces fewer side effects and achieves better results.

A medicated stent may be fabricated by coating the surface of either a metallic or polymeric scaffolding with a polymeric carrier that includes an active or bioactive agent or drug. Polymeric scaffolding may also serve as a carrier of an active agent or drug.

The stent must be able to satisfy a number of mechanical requirements. The stent must be capable of withstanding the structural loads, namely radial compressive forces, imposed on the stent as it supports the walls of a vessel. Therefore, a stent must possess adequate radial strength. Radial strength, which is the ability of a stent to resist radial compressive forces, relates to a stent's radial yield strength and radial stiffness around a circumferential direction of the stent. A stent's "radial yield strength" or "radial strength" (for purposes of this application) may be understood as the compressive loading, which if exceeded, creates a yield stress condition resulting in the stent diameter not returning to its unloaded diameter, i.e., there is irrecoverable deformation of the stent. When the radial yield strength is exceeded the stent is expected to yield more severely and only a minimal force is required to cause major deformation.

Once expanded, the stent must adequately maintain its size and shape throughout its service life despite the various forces that may come to bear on it, including the cyclic loading induced by the beating heart. For example, a radially directed force may tend to cause a stent to recoil inward. In addition, the stent must possess sufficient flexibility to allow for crimping, expansion, and cyclic loading.

Some treatments with stents require its presence for only a limited period of time. Once treatment is complete, which may include structural tissue support and/or drug delivery, it may be desirable for the stent to be removed or disappear from the treatment location. One way of having a stent disappear may be by fabricating a stent in whole or in part from materials that erodes or disintegrate through exposure to conditions within the body. Stents fabricated from biodegradable, bioabsorbable, and/or bioerodable materials such as bioabsorbable polymers can be designed to completely erode only after the clinical need for them has ended.

However, there are several challenges making a bioabsorbable polymeric stent. These include making a stent with sufficient radial strength, stiffness, and toughness or resistance to fracture. Another challenge is maintaining the properties of the finished stent from the end of manufacturing to the time of implantation. Medical devices are typically stored for an indefinite or variable period of time after fabrication. Since storage time will vary for each device that is made, the problem of product consistency arises if properties change over time.

INCORPORATION BY REFERENCE

All publications and patent applications mentioned in this specification are herein incorporated by reference to the same extent as if each individual publication or patent application was specifically and individually indicated to be incorporated by reference, and as if each said individual publication or patent application was fully set forth, including any figures, herein.

SUMMARY OF THE INVENTION

Various embodiments of the present invention include a method of making a stent, comprising: providing a polymeric stent scaffolding disposed on a catheter; exposing the scaffolding to E-beam radiation for sterilization, wherein the scaffolding is exposed to a gas containing oxygen during the exposure, wherein an oxygen content of the gas is greater than 1%; and packaging the scaffolding in an inert gas environment.

Further embodiments of the present invention include a method of making a stent, comprising: providing a polymeric stent scaffolding disposed on a catheter, wherein the scaffolding is sealed in a package permeable to and comprising air; and exposing the packaged scaffolding to E-beam radiation for sterilization; after the radiation exposure, disposing package in a gas impermeable package, wherein oxygen in the air quenches free radicals generated by the radiation exposure;

removing the air from the packages; and filling the packages with an inert gas and sealing the packages.

Additional embodiments of the present invention include a method of making a stent, comprising: providing a polymeric stent scaffolding; exposing the scaffolding to E-beam radiation for sterilization, wherein the scaffolding is exposed to an inert gas environment during sterilization; exposing the irradiated scaffolding to air to quench free radicals generated by the radiation exposure and stabilize a molecular weight of the scaffolding polymer; and after the period of time, storing scaffolding in an inert gas environment.

Other embodiments of the present invention include a method of making a stent, comprising: providing a package having an inner gas permeable layer and an outer gas impermeable layer, wherein the inner layer and the outer layer have an inert gas environment within and the inner layer and outer layer are sealed, wherein a polymer scaffolding is disposed within the inner layer; exposing the scaffolding to E-beam radiation for sterilization; allowing fluid communication between ambient air and the outer layer to expose the scaffolding to air for a period of time; after the period of time, removing air from and sealing the gas impermeable package; and storing the scaffolding in an inert gas environment.

Further embodiments of the present invention include a method of making a stent, comprising: providing a polymeric stent scaffolding; exposing the scaffolding to E-beam radiation for sterilization, wherein during the exposure the scaffolding is in a sealed gas impermeable package containing a gas mixture of oxygen and an inert gas, wherein the oxygen content of the gas mixture is 1% or less; and storing the scaffolding in the gas mixture until use of the scaffolding, wherein the oxygen in the gas mixture quenches free radicals in the scaffolding polymer and stabilizes the molecular weight of the scaffolding polymer.

Additional embodiments of the present invention include a method of making a stent, comprising: providing a polymeric stent scaffolding; selecting a final Mn of the polymer of the scaffolding; irradiating the scaffolding with E-beam radiation for sterilization in an inert gas environment, wherein the polymer of the scaffolding has an initial Mn after the irradiation; allowing the Mn of the irradiated scaffolding to increase from the initial Mn to the final Mn in the inert gas environment; exposing the scaffolding to an oxygen-containing gas to stabilize the Mn of the scaffolding at the final Mn; and storing the stabilized scaffolding in an inert gas environment.

Further embodiments of the present invention include a method of making a stent, comprising: providing a package having a first side that is impermeable and a second side that is gas permeable, wherein the first side has an inert gas environment within and the second side has ambient air, wherein a polymeric scaffolding is disposed within the first side, where the sides are connected by a movable sealer that allows movement of the scaffolding from the first side to the second side without fluid communication between the sides; exposing the scaffolding to E-beam radiation for sterilization; after a period of time after sterilization, shifting the scaffolding with the movable sealer to the second side to expose the stent to air; and after a selected stabilization time, shifting the scaffolding to the first side to the inert gas environment; and resealing the first side with inert gas.

Additional embodiments of the present invention include a method of making a stent, comprising: providing a package having a first side and a second side that are both gas impermeable, wherein the first side has an inert gas environment and the second side has a mixture of an inert gas and oxygen, wherein a polymeric scaffolding is disposed within the first side, wherein the sides are connected by a valve that allows fluid communication between the first side to the second side when the valve is open; exposing the scaffolding to E-beam radiation for sterilization; after a period of time after sterilization, opening the valve to allow fluid communication between the first side and the second side to expose the scaffolding to oxygen and terminate free radicals in the scaffolding; and after a selected stabilization time, closing the valve and replacing the inert gas and mixture in the first side with an inert gas environment.

DETAILED DESCRIPTION OF THE INVENTION

Various embodiments of the present invention relate to manufacture of polymeric implantable medical devices. In particular, the embodiments include methods of stabilizing the properties of polymer stents after radiation sterilization.

The methods described herein are generally applicable to any amorphous or semi-crystalline polymeric implantable medical device, especially those that have load bearing portions when in use or have portions that undergo deformation during use. In particular, the methods can be applied to tubular implantable medical devices such as self-expandable stents, balloon-expandable stents, and stent-grafts.

Figure 1:
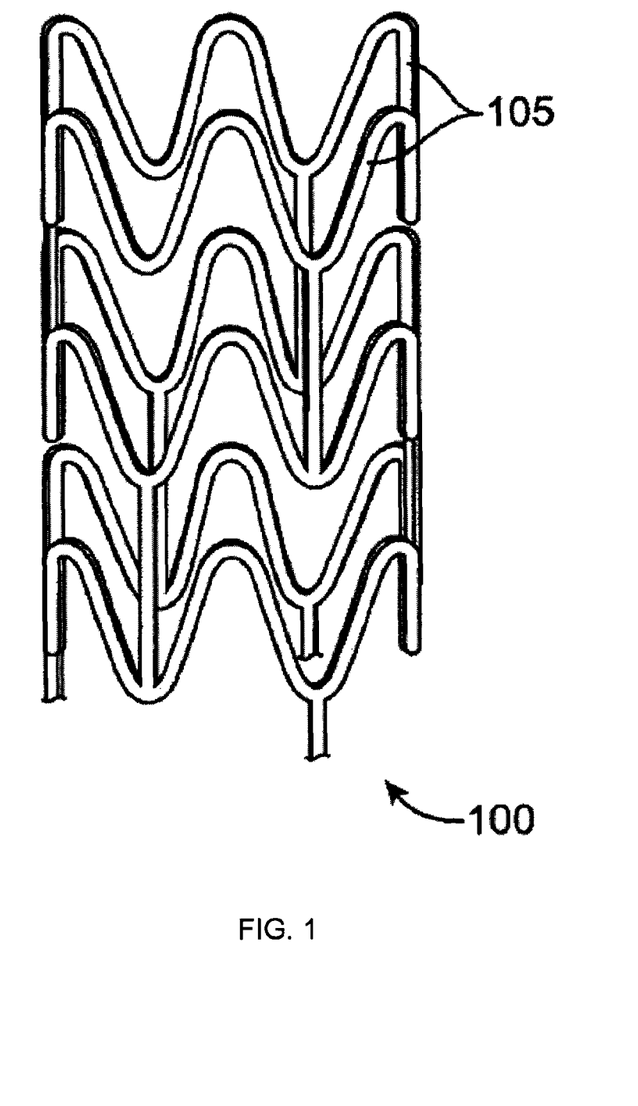
FIG. 1 depicts a stent.

A stent may include a pattern or network of interconnecting structural elements or struts. FIG. 1 depicts a view of a stent 100. In some embodiments, a stent may include a body, backbone, or scaffolding having a pattern or network of interconnecting structural elements 105. Stent 100 may be formed from a tube (not shown). The structural pattern of the device can be of virtually any design. The embodiments disclosed herein are not limited to stents or to the stent pattern illustrated in FIG. 1. The embodiments are easily applicable to other patterns and other devices. The variations in the structure of patterns are virtually unlimited.

A stent such as stent 100 may be fabricated from a polymeric tube or a sheet by rolling and bonding the sheet to form the tube. A tube or sheet can be formed by extrusion or injection molding. A stent pattern, such as the one pictured in FIG. 1, can be formed in a tube or sheet with a technique such as laser cutting or chemical etching. The stent can then be crimped on to a balloon or catheter for delivery into a bodily lumen.

An implantable medical device of the present invention can be made partially or completely from a biodegradable, bioresorbable, bioabsorbable, or biostable polymer. A polymer for use in fabricating an implantable medical device can be biostable, bioresorbable, bioabsorbable, biodegradable or bioerodable. Biostable refers to polymers that are not biodegradable. The terms biodegradable, bioresorbable, bioabsorbable, and bioerodable are used interchangeably and refer to polymers that are capable of being completely degraded and/or eroded into different degrees of molecular levels when exposed to bodily fluids such as blood and can be gradually resorbed, absorbed, and/or eliminated by the body. The processes of breaking down and absorption of the polymer can be caused by, for example, hydrolysis and metabolic processes.

A stent made from a biodegradable polymer is intended to remain in the body for a duration of time until its intended function of, for example, maintaining vascular patency and/or drug delivery is accomplished. After the process of degradation, erosion, absorption, and/or resorption has been completed, no portion of the biodegradable stent, or a biodegradable portion of the stent will remain. In some embodiments, very negligible traces or residue may be left behind.

The duration of a treatment period depends on the bodily disorder that is being treated. In treatments of coronary heart disease involving use of stents in diseased vessels, the duration can be in a range from several months to a few years. The duration is typically up to about six months, twelve months, eighteen months, or two years. In some situations, the treatment period can extend beyond two years.

As indicated above, a stent has certain mechanical requirements such as high radial strength, high stiffness or high modulus, and high fracture toughness. A stent that meets such requirements greatly facilitates the delivery, deployment, and treatment of a diseased vessel. With respect to radial strength and stiffness, a stent must have sufficient radial strength to withstand structural loads, namely radial compressive forces, imposed on the stent so that the stent can supports the walls of a vessel at a selected diameter for a desired time period. A polymeric stent with inadequate radial strength and/or stiffness can result in an inability to maintain a lumen at a desired diameter for a sufficient period of time after implantation into a vessel.

In addition, the stent must possess sufficient toughness or resistance to fracture to allow for crimping, expansion, and cyclic loading. These aspects of the use of the stent involve deformation of various portions of the stent. Sufficient toughness is important to prevent cracking or fracture during use which could lead to premature mechanical failure of the stent.

The strength to weight ratio of polymers is usually smaller than that of metals. To compensate for this, a polymeric stent can require significantly thicker struts than a metallic stent, which results in an undesirably large profile. The strength deficiency of polymers is addressed in the present invention by incorporating a deformation step in the stent fabrication process by subjecting the polymer construct to deformation. Deforming polymers tends to increase the strength along the direction of deformation, which is believed to be due to the induced polymer chain orientation along the direction of deformation. For example, radial expansion of a polymeric tube construct provides preferred circumferential polymer chain orientation in the tube. Additionally, stretching a tube provides preferred axial orientation of polymer chains in the tube. Thus, a stent fabrication process can include radially deforming a polymer tube and cutting a stent from the deformed tube. The deformation process also results in strain induced crystallization, increasing the crystallinity of the construct which increases the strength of the polymer.

Semi-crystalline polymers that are stiff or rigid under biological conditions or conditions within a human body are particularly suitable for use as a scaffolding material. Specifically, polymers that have a glass transition temperature (Tg) sufficiently above human body temperature which is approximately 37° C., should be rigid upon implantation. Poly(L-lactide) (PLLA) is an example of such a polymer. These polymers, however, may exhibit a brittle fracture mechanism in which there is little or no plastic deformation prior to failure. As a result, it is important not only to improve the strength of such polymers when making a device, but also to improve the fracture toughness for the range of use of a stent, specifically for the range deformation during use of the stent. In particular, it is important for a stent to have high resistance to fracture throughout the range of use of a stent, i.e., crimping, delivery, deployment, and during a desired treatment period after deployment.

Exemplary biodegradable polymers for use with a bioabsorbable polymer scaffolding include poly(L-lactide) (PLLA), poly(D-lactide) (PDLA), polyglycolide (PGA), and poly(L-lactide-co-glycolide) (PLGA). With respect to PLGA, the stent scaffolding can be made from PLGA with a mole % of GA between 5-15 mol %. The PLGA can have a mole % of (LA:GA) of 85:15 (or a range of 82:18 to 88:12), 95:5 (or a range of 93:7 to 97:3), or commercially available PLGA products identified being 85:15 or 95:5 PLGA.

The fabrication methods of a bioabsorbable stent for use in the methods of treatment described herein can include the following steps:

(1) forming a polymeric tube using extrusion,
(2) radially deforming the formed tube,
(3) forming a stent scaffolding from the deformed tube by laser machining a stent pattern in the deformed tube with laser cutting,
(4) optionally forming a therapeutic coating over the scaffolding,
(5) crimping the stent over a delivery balloon, and
(6) sterilization with election-beam (E-beam) radiation.

In step (2) above, the extruded tube may be radially deformed to increase the radial strength of the tube, and thus, the finished stent. The increase in strength reduces the thickness of the struts required to support a lumen with the stent when expanded at an implant site. In exemplary embodiments, the strut thickness can be 100-200 microns, or more narrowly, 120-180, 130-170, or 140-160 microns.

Detailed discussion of the manufacturing process of a bioabsorbable stent can be found elsewhere, e.g., U.S. Patent Publication No. 20070283552, which is incorporated by reference herein.

A packaged stent and catheter are sterilized to reduce the bioburden of the stent and delivery system to a specified level. Bioburden refers generally to the number of microorganisms with which an object is contaminated. The degree of sterilization is typically measured by a sterility assurance level (SAL) which refers to the probability of a viable microorganism being present on a product unit after sterilization. The required SAL for a product is dependent on the intended use of the product. For example, a product, such as a stent, to be used in the body's fluid path is considered a Class III device and requires an SAL of $10^{-6}$. SAL's for various medical devices can be found in materials from the Association for the Advancement of Medical Instrumentation (AAMI) in Arlington, Va.

A stent is typically sterilized after mounting the stent at the end of a catheter by crimping. Prior to sterilization, the stent-catheter assembly is placed in a package and sealed. The package is typically made of a gas-impermeable material such as aluminum foil. The package remains sealed after sterilization until the time of implantation. The interior of the packaging is typically an inert gas such as argon.

An inert gas refers generally to a non-reactive gas. Inert gases include noble gases such as argon and helium. Inert gases also include compound gases that are non-reactive due to the valence, the outermost electron shell, being complete, such as diatomic nitrogen. The inert gas environment or atmosphere may have 0% oxygen or may contain a small amount of oxygen, for example, less than 0.01%, 0.005%, 0.002, or less than 0.001% oxygen. The content of gases is expressed in mole percent, unless otherwise specified.

The packaging of the stent in an inert gas may be achieved by vacuum evacuation of the packaging followed by a backfill of the packaging with an inert gas such as argon. The evacuation and backfill process can be repeated to assure complete removal of oxygen. The final oxygen content of the packaging atmosphere may be approximately 0.002% or less, 0.002% to 0.01%, 0.01% to 0.015%, 0.015% to 0.02%, or 0.02% to 0.04%.

The packaging is designed to prevent exposure of the stent to any bioburden such as bacteria as well as non-inert gases such as oxygen as well as moisture. Oxygen and moisture may adversely affect the properties of a drug delivery coating, and thus, the drug delivery profile. Additionally, moisture can also cause degradation of the scaffolding. Unless otherwise specified, "oxygen" refers to diatomic oxygen. Irradiation can convert diatomic oxygen to ozone, which can quench free radicals.

The sterilization can be performed by exposing the stent and catheter to radiation, for example, electron beam (E-beam), gamma ray, and x-ray sterilization. A sterilization dose can be determined by selecting a dose that provides a required SAL. A sample can be exposed to the required dose in one or multiple passes. An exemplary radiation dose for sterilization of a stent may be 20-50 kGy or any value between, for example, 25 kGy.

During E-beam irradiation of a bioabsorbable scaffolding, such as a PLLA scaffolding, energy is deposited uniformly across the device. The irradiation leads to polymer chain scission, excitation of the macromolecules, and the formation of free radicals. Free radicals refer to atomic or molecular species with unpaired electrons on an otherwise open shell configuration. Free radicals can be formed by oxidation reactions. These unpaired electrons are usually highly reactive, so free radicals are likely to take part in chemical reactions, including chain reactions. These free radicals generated proceed to react with each other or initiate further reactions within the polymer chains. The outcomes of these reactions will be recombination, branching, crosslinking, chain scission, or propagation.

The immediate effect of the irradiation arises from chain scission since a decrease in molecular weight is observed after exposure to the radiation. For example, a PLLA stent scaffolding with a number average molecular weight (Mn)=260 kDa before E-beam sterilization decreases to an Mn between 70-80 kDa immediately after a radiation dose of 27.5 kGy. The immediate decrease in the molecular weight is not generally a problem, as long at the molecular weight after sterilization is at a desired level. A desired post-sterilization molecular weight may be obtained by adjusting the molecular weight resin. The Mn of a PLLA scaffolding post-sterilization may be 60 to 65 kDa, 65-70 kDa, 70 to 80 kDa, or 80 to 90 kDa.

Thus, it was known to the inventors that radiation sterilization of a bioabsorbable stent scaffolding causes a drop in molecular weight immediately after exposure. It was also known that radiation sterilization causes the generation of free radicals in the polymer. However, decay mechanism of the free radicals in the polymer scaffolding was not. Nor was the impact of the free radicals or radiation sterilization in general on stent properties, beyond the immediate changes, over a longer term (e.g., hours, days, weeks, months after irradiation.

Given the potential of free radicals to alter the long term properties of a bioabsorbable polymer scaffolding, it is important to accurately detect free radical type, level, and especially its change with time after sterilization. This offers very valuable information for design and modification of a bioabsorbable polymer scaffolding.

Electron spin resonance spectroscopy (ESR) technique has been used for the detection of free radicals. The original implementation of this method originally used by the inventors was used commonly in various industrial applications. According to that original method, a stent is sterilized in an inert gas environment in a pouch, the stent is taken out of the pouch, and stored in a glass container. Then the information about free radical level, type and its change with time is detected and estimated based on measurement of the spins of unpaired electrons in a magnetic field. All the previous ESR results based on this original method showed that the half-life of the generated free radicals is very short, and therefore, based on these results would not be expected to cause any significant impact on final stent product properties.

The inventors then considered a hypothesis that sample storage gas environment might have a potential impact on free radical decay. While the stent scaffolding is stored in an argon sealed pouch prior to implantation, the test samples in the original ESR method were stored in a regular glass container filled with air.

The inventors considered whether ESR measurement methods that would mimic the storage environment would show a free radical decay profile different from the original method. In one alternative method, the ESR measurements may be performed on a sample in a specially designed container filled with an inert gas such as argon. Such a method may mimic the real packaging environment in the pouch.

Another alternative method was applied to generating a free radical decay profile of irradiated PLLA scaffolding. In this method, a set of irradiated samples were stored in separate sealed gas impermeable aluminum pouches. The samples were taken out of a pouch at different times. After a sample was taken out of pouch, it would immediately be placed in the ESR equipment for free radical detection. By running ESR using samples stored in the argon sealed pouch at different times and collecting all received data together, a free radical decay profile was obtained.

Figure 2:
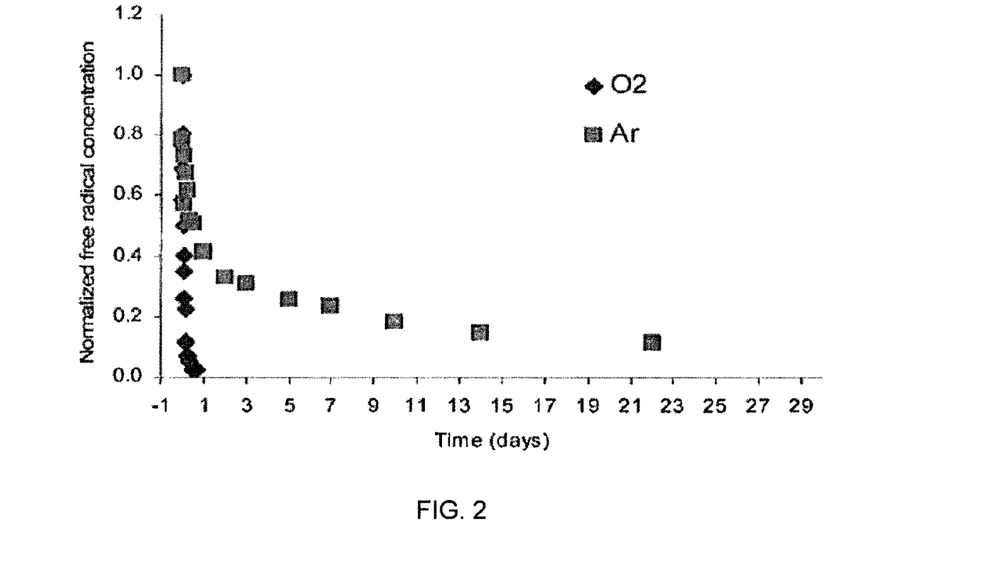
FIG. 2 depicts a normalized free radical decay profile of PLLA scaffolding samples stored under different environments (argon vs. oxygen) after E-beam sterilization in argon.

Free radical decay profiles for PLLA scaffoldings sterilized in an inert argon atmosphere were generated according to the alternative method described above. The results surprisingly show the presence of moderately persistent free radicals. FIG. 2 depicts a normalized free radical decay profile of E-beam irradiated PLLA scaffolding using the alternative method of samples aged in a sealed pouch with argon. FIG. 2 also shows free radical decay profile of samples aged in air. The results from the alternative method in FIG. 2 clearly show that the free radicals exist in the scaffolding more than 3 weeks after electron beam processing of the scaffolds while in the samples exposed to air, the free radicals decay to near zero in about 1 day.

During the relatively long period of free radical decay in the former, it is believed that the free radicals are related to temporal changes in molecular weight, thereby increasing variability of the product. Measurements according to the original method show that a decay to zero in about 1 day, and thus is not a reflection of the decay of a PLLA scaffolding in an inert gas environment.

Figure 3:
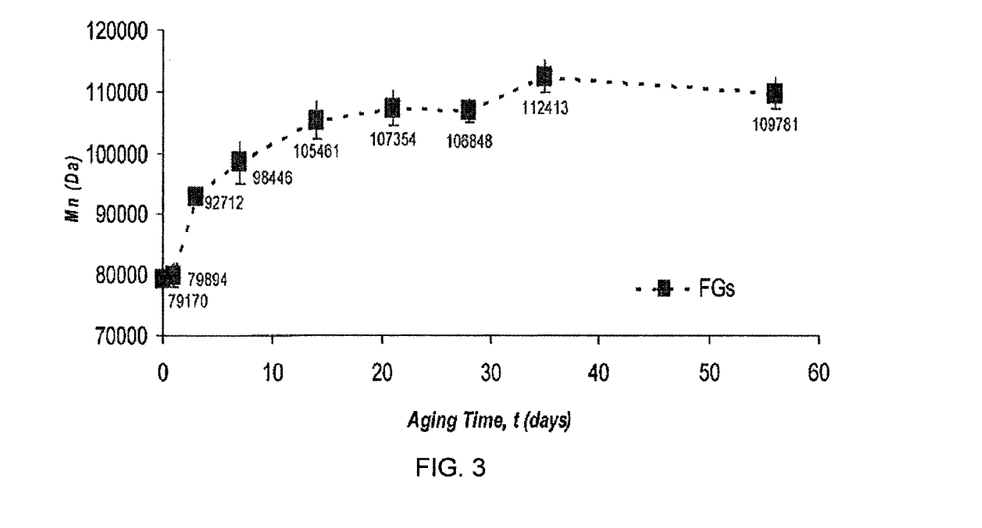
FIG. 3 depicts the Mn versus time of a PLLA scaffolding after radiation sterilization aged in argon.

These results showed that the long term free radical decay might cause continued molecular weight change of scaffolding after E-beam sterilization. The inventors have found surprisingly the molecular weight of a PLLA scaffolding continues to increase up to about 40 days after E-beam sterilization. FIG. 3 depicts the Mn versus time of a PLLA scaffolding after radiation sterilization with a dose of 27.5 kGy and aged in argon. As indicated above, the Mn is shown to increase from an initial value after radiation exposure to about 110 kDa 40 days after exposure. The decay profile of the free radicals suggests the molecular weight change may be associated with free radicals generated from sterilization.

The significance of the time scale of such changes is the impact on product consistency. It is desired generally for the properties of a medical device to be independent of the storage time. More importantly, it is desirable for the performance of the device to be independent of storage time. Changes in some properties may not significantly affect the performance of the device, while other changes may.

The consistency of molecular weight at implantation is important since the inventors have recognized that the initial molecular weight, specifically Mn, is a major component in determining the degradation profile of the scaffolding. In order to heal a diseased vessel, a scaffolding must have a proper degradation profile. The scaffolding should maintain radial strength for a period of time to allow healing of the vessel. After this period, the scaffolding radial strength may decrease and the stent should absorb away as quickly and safely as possible. The inventors have found that molecular weight is one of several variables that impact total resorption time. Increasing the consistency of molecular weight will therefore reduce variability in the total resorption time.

One way to address the product stability and consistency issue, or equivalently, addressing the control of the post-sterilization molecular weight change, is to condition a sterilized final product for a period of time after sterilization prior to release. For example, the product may be conditioned 3 weeks at room temperature or 7-10 days at an elevated temperature such as 30° C. This conditioning would stabilize the Mn or level off Mn change before release of the product. In this case, the properties of the released product would be stable, but the conditioning would result only in a molecular weight at the final high end.

Various embodiments of the present invention include methods of stabilizing the properties of a polymeric stent scaffolding and coating and preventing changes in properties as a function of time caused by radiation sterilization. The methods include exposing the scaffolding to oxygen during, after, or both during and after radiation sterilization to stabilize molecular weight and other properties. The exposure may be and is desirable performed in a manner that preserves the degree of sterility of the stent or reduction in bioburden of the stent provided by the radiation sterilization. The sterility can be maintained by allowing the oxygen exposure through a gas permeable material or package that allows gas permeation while prevent permeation of bioburden. Exposure to oxygen or oxygen-containing gas according to the present invention does not refer to exposure to a gas with a residual oxygen content, for example, in evacuated and inert gas backfilled containers typically used for post-sterilization storage which can be about 0.002% or less oxygen content.

Exposing sterilized stents to oxygen is contrary the generally accepted practice in the art which focuses on isolating pre- and post-sterilized stent from non-inert environment, e.g., reactive gases and moisture. Specifically, it is believed that exposing stents to atmospheric levels of oxygen causes may cause an additional drop in the molecular weight of PLLA. As used herein, "oxygen" refers to diatomic oxygen, $O_2$. Stabilizing the molecular weight may refer to less than a 10% change in Mn over a period after radiation exposure of at least 30 days, 30 to 60 days, or greater than 60 days.

The inventors have found from several studies that exposing the stent scaffolding to an oxygen-containing gas such as air during or after radiation exposure reduces or prevents further changes in molecular weight and other properties with time. It is believed from these studies that oxygen reacts with the free radicals which renders the free radicals non-reactive or terminates the free radicals. Therefore, the free radicals react with and are terminated by the oxygen rather than reacting with the polymer chains of the stent polymer. The termination or quenching of the free radicals occurs over a much shorter time frame than the decay of the free radicals in an inert environment.

In certain embodiments of the present invention, a method of making a stent includes providing a stent-catheter assembly including a polymeric stent scaffolding disposed on a catheter. The scaffolding is exposed to radiation, such as E-beam radiation, to sterilize. The scaffolding is exposed to an oxygen-containing gas during the radiation sterilization. For example, the stent-catheter assembly is exposed to air. The oxygen-containing gas may be sufficient to quench or terminate all or all but a residual amount (e.g., less than $5 \times 10^7$ DI/mg) of the free radicals in a short period of time, for example, in less than 1 hr, 5 hrs, 12 hrs, 1 day, 2 days, or less than 5 days. The exposure to oxygen-containing gas can continue for a period of time after the radiation exposure, for example, until the free radicals are terminated, equivalently, the free radicals have decayed to zero or below a level at which the molecular weight of the scaffolding polymer is stabilized for a long term, such as 2 weeks, 1 month, or longer than 1 month. The stent may then be stored in an inert gas atmosphere indefinitely, for example, until implantation. An exemplary molecular weight profile according to these embodiments is illustrated by study D in Table 1 and FIG. 9.

Figure 4:
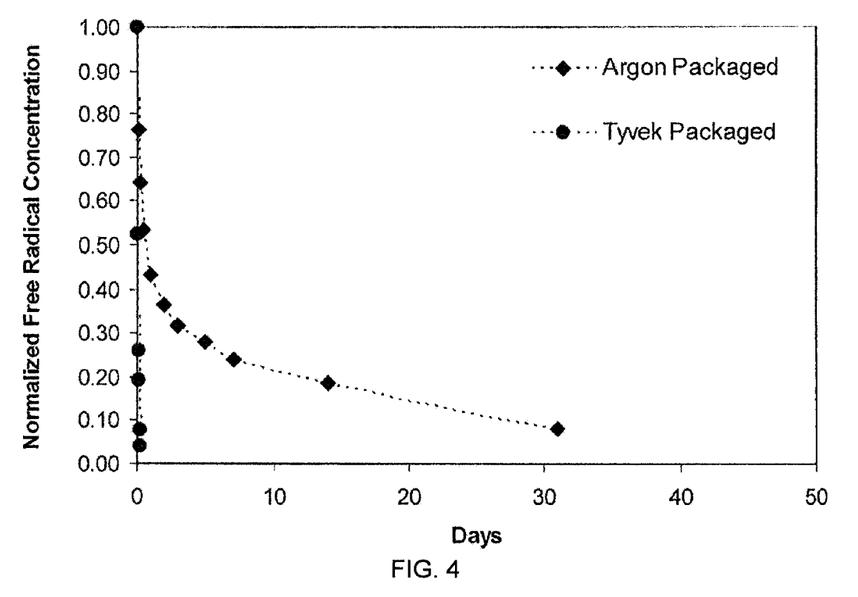
FIG. 4 depicts a normalized free radical decay of E-beam irradiated PLLA scaffolding samples sterilized and aged in a sealed foil pouch in argon and samples sterilized and aged in a Tyvek® pouch.

FIG. 4 depicts the free radical decay profiles of irradiated PLLA scaffolding for two cases, (1) sterilized in a sealed foil pouch in argon and (2) sterilized and aged in a gas permeable Tyvek® pouch, thus exposed to air. The Tyvek® pouch allows permeation of air, while preserving sterility. The expanded time scale compared to FIG. 2 illustrates the dramatic unexpected difference in the decay of free radicals in an inert atmosphere compared to an oxygen-containing environment.

Figure 5A:
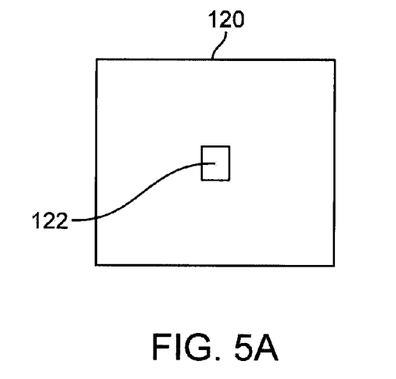
FIG. 5A depicts a schematic representation of a Tyvek® pouch with a stent contained within.
Figure 5B:
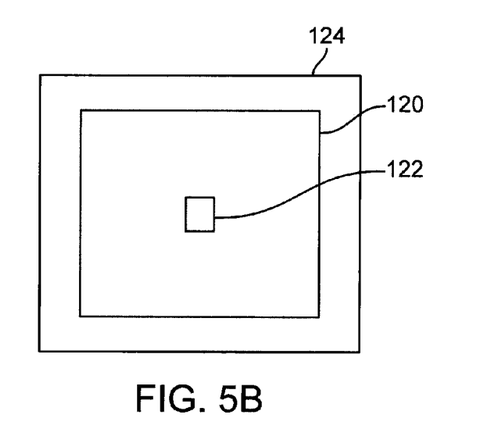
FIG. 5B depicts the Tyvek® pouch of FIG. 5B disposed within an aluminum pouch.

The above stabilization methods may be accomplished in a number of ways. In an exemplary embodiment, in a first step, prior to sterilization, the stent is placed in a gas permeable pouch such as a Tyvek® pouch. FIG. 5A depicts a schematic representation of a Tyvek® pouch 120 with a stent 122 contained within. The pouch will allow oxygen to pass through to terminate any free radicals generated during sterilization to prevent any post-sterilization molecular weight change associated with free radicals, while preserving the sterility level of the stent. Materials other than Tyvek® that are gas permeable and that also preserve a sterility level may be used in this embodiment and others described herein. Although the pouch is permeable to air, it will block the permeation of bioburden to maintain the sterility level post-sterilization. The stent may be kept in the pouch a period of time until the molecular weight of the scaffolding polymer of the stent is stabilized by the oxygen exposure. In a second step, the gas permeable pouch can be disposed within a gas impermeable pouch, such as an aluminum pouch. FIG. 5B depicts Tyvek® pouch 120 disposed within aluminum pouch 124. The gas impermeable pouch may then be evacuated, backfilled with an inert gas, and sealed for long term storage or until implantation.

Other embodiments of the present invention include exposing the scaffolding to radiation in an inert gas environment. Following radiation exposure in the inert gas environment, the scaffolding is exposed to an oxygen-containing gas. The exposure the oxygen-containing gas can continue for a period of time after the radiation exposure. The period of time may be sufficient to prevent any further molecular weight change. The stent may then be stored in an inert gas atmosphere indefinitely, for example, until implantation. An exemplary molecular weight profile according to these embodiments is illustrated by study E in Table 1 and FIG. 9.

Figure 9:
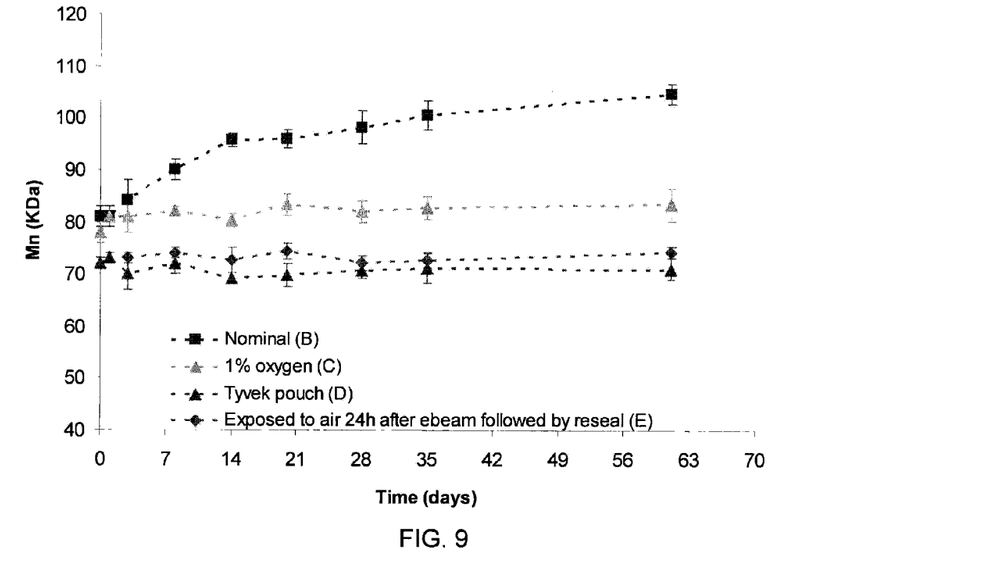
FIG. 9 depicts the Mn versus time for irradiated PLLA scaffolding samples under different packaging environments.

The inventors have observed that exposure of polymer scaffolding to air during sterilization results in a greater drop in Mn than sterilization in an inert gas environment (see FIG. 9). E-beam radiation in a gas with high oxygen content may generate ozone which is highly reactive and can react with polymer chains of the stent or with a drug in the stent.

Figure 6:
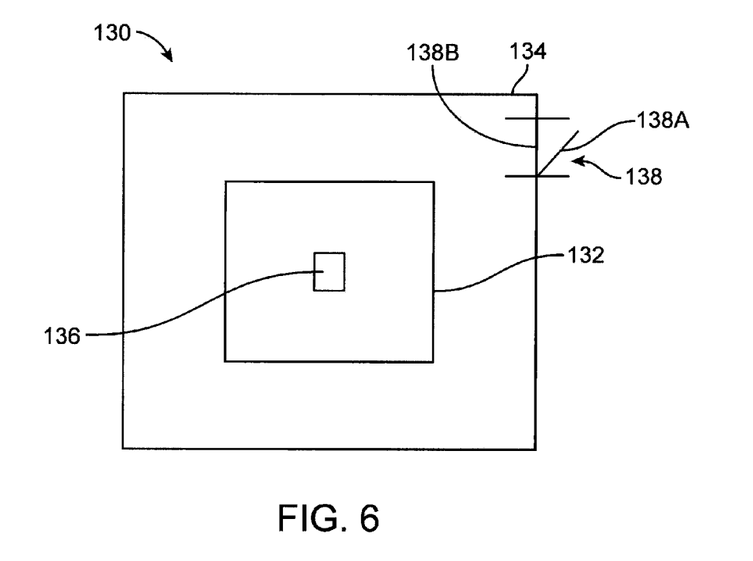
FIG. 6 depicts a schematic representation of a double-layered pouch.

These other embodiments involving exposure to oxygen-containing gas after radiation exposure may be accomplished in a variety of ways. In an exemplary embodiment, a method involves packaging a stent in a double-layered pouch. The first or inner layer is gas permeable, such as a Tyvek® pouch, and the second or outer layer is gas impermeable, such as an aluminum pouch. FIG. 6 depicts a schematic representation of a double-layered pouch 130. Pouch 130 has an inner gas permeable Tyvek® layer 132 and an outer gas impermeable aluminum layer 134. Stent 136 is disposed within the inner Tyvek® layer. Prior to and during E-beam sterilization the outer layer is sealed and contains an inert gas environment ant the stent is sealed within the Tyvek® layer, also in an inert gas environment. Post-sterilization, the aluminum layer is opened, or more generally, fluid communication is allowed between the outer pouch and ambient air to allow air into the pouches, which exposes the stent to air. Outer pouch 134 has a sealable opening 138 that can be open and closed to allow exposure to air and sealed from exposure to air, respectively. For example, sealable opening 138 has a foil seal 138A and a Tyvek® window 139B that allows air to enter pouch 134. The stent is exposed to the air for at least a period of time to stabilize the molecular weight of the stent scaffolding polymer. The foil pouch may then be backfilled with inert gas and resealed. Alternatively, an additional foil pouch may be added outside of the double layer pouch, evacuated, backfilled with inert gas, and resealed.

The inventors have found that the cumulative free radicals terminated depend on the time of exposure to the oxygen-containing gas. Thus, the oxygen exposure may continue until the concentration of free radicals levels decays below a selected value. For example, the selected concentration can be $5 \times 10^7$ DI/mg.

Following the exposure to oxygen for the period of time, the scaffolding may then be disposed into an inert gas environment or the gas may be removed from the packaged backfilled with an inert gas.

The oxygen-containing gas can have any concentration of oxygen that stabilizes (e.g., within 10%) the molecular weight (Mn) as observed over a period of at least 2 weeks, 1 month, or 2 months. Alternatively or additionally, the oxygen-containing can have any concentration of oxygen that causes the free radical concentration to decay to below a certain level (e.g., $5 \times 10^7$ DI/mg) in less than 1 hr, 5 hrs, 12 hrs, 1 day, 2 days, or less than 5 days.

For example, air may be used which is 20.95 mol % oxygen. The balance of the gas can include an inert gas(s) and possible other residual gas impurities. The concentration of oxygen in the gas can be less than 1%, 1 to 5%, 5-10%, more than 10% to air concentration, air concentration to 40 mol %, 40 to 60%, 60 to 90%, 90-95%, or greater than 95%.

The inventors also found that the rate of free radical decay depends on the concentration of oxygen. The lower the concentration of oxygen, the longer the time required to reach a given concentration of free radicals. Exemplary exposure times may be less than 10 min, 10 min to 1 hr, 1 to 3 hr, 3 to 6 hr, 6 to 9 hr, 9 to 12 hr, 12 hr to 1 day, 1 to 2 days, 2 to 3 days, 3 to 5 days, or greater than 5 days.

In further embodiments, the stent may be packaged and stored until release and implantation in an atmosphere that is a mixture of inert gas and oxygen. The mixture is primarily an inert gas with a very low oxygen content that is substantially lower than that of air, but greater than the residual content of an evacuated and inert gas backfilled package. The packaged stent may then be radiation sterilized and stored in the atmosphere indefinitely, for example, until release and implantation. "Release" refers to release or shipping from a manufacturer or contractor of the manufacturer in a ready-to-implant condition. The storage time from sterilization may be 1 to 10 days, 10 days to 1 month, 1 to 3 months, 3 to 6 months, 6 months to 1 year, 1 to 2 years. The concentration of oxygen in the gas mixture may be high enough to cause the free radical concentration to decay to below a certain level (e.g., $5 \times 10^7$ DI/mg) in less than 5 hrs, 12 hrs, 1 day, 2 days, or less than 5 days. The concentration of oxygen should be low enough that storage for any of the storage ranges disclosed will not result in adverse effects on the molecular weight of the polymer of the stent or drug. In exemplary embodiments, the content of oxygen may be less than 0.5%, 0.5 to 1%, 1 to 2%, 0.08 to 1.02%, 2 to 3%, 3 to 5%, 5 to 10%, less than 1%, less than 5%, less than 10%, or 10 to 20%.

In some embodiments, prior to sterilization, the scaffold is placed in a gas mpeuneable package and the atmosphere in the package, i.e., air, may be evacuated and then the package may be backfilled with the inert gas-oxygen mixture. For example, the same equipment may be used as that for evacuating and backfilling the package with inert gas, which backfills the package from an argon cylinder. In the present invention, the package may be backfilled with the inert gas/oxygen mixture with the controlled amount of oxygen. The molecular weight profile according to these embodiments is illustrated by study C in Table 1 and FIG. 9.

Figure 7:
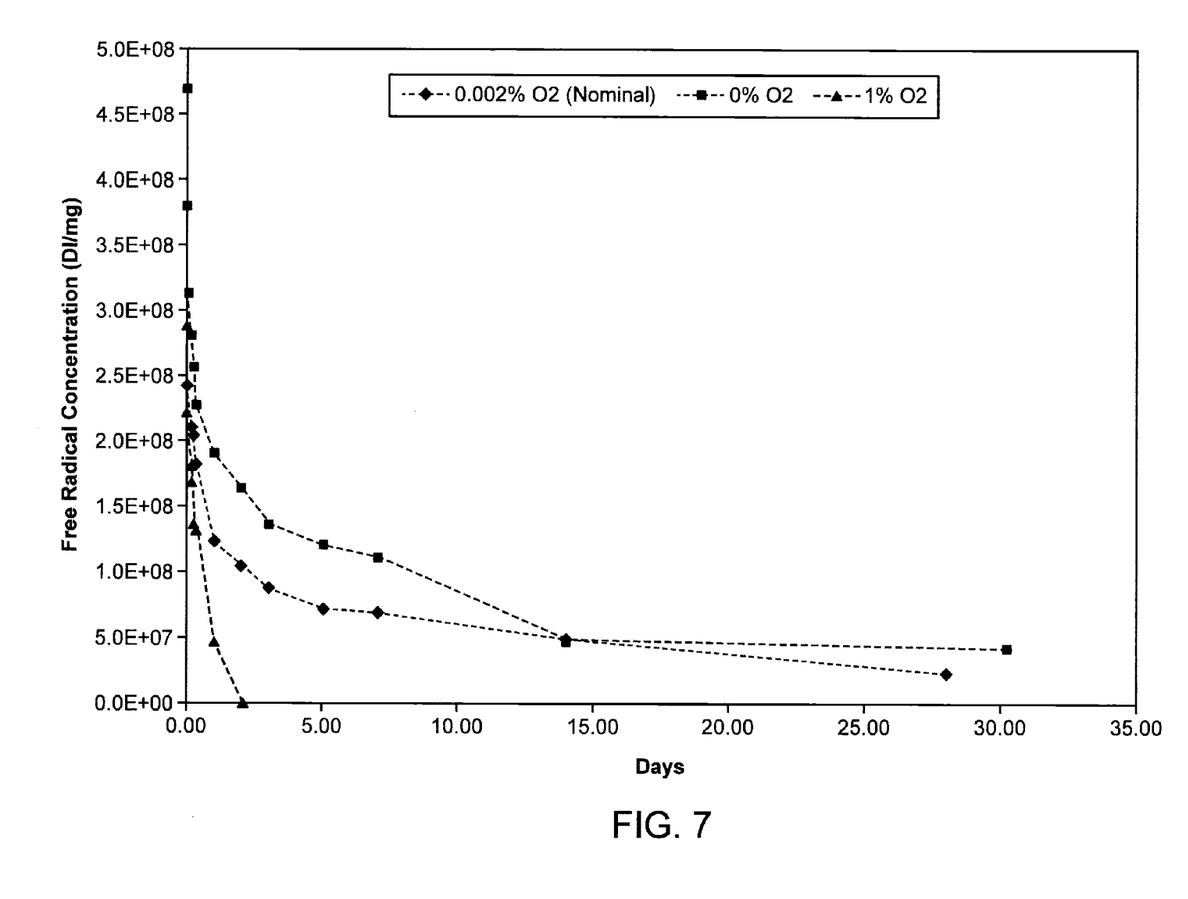
FIG. 7 depicts the free radical decay in irradiated PLLA scaffolding samples sterilized and stored in containers with different oxygen concentrations, 0%, 0.002%, and 1%.

Studies have shown for a gas mixture with an oxygen content of 1% that no free radicals can be detected after 2 days, whereas a signal is still detected at 28 days using an inert gas atmosphere. FIG. 7 depicts the free radical decay in irradiated PLLA scaffolding samples sterilized and stored in containers with different oxygen concentrations, 0%, 0.002%, and 1%. The free radical decay of samples in 0.002% oxygen is more rapid than the 0% oxygen, but the long term decay is similar. The free radical decay of the samples in 1% oxygen samples is significantly faster than in the 0% or 0.002% oxygen.

Figure 8:
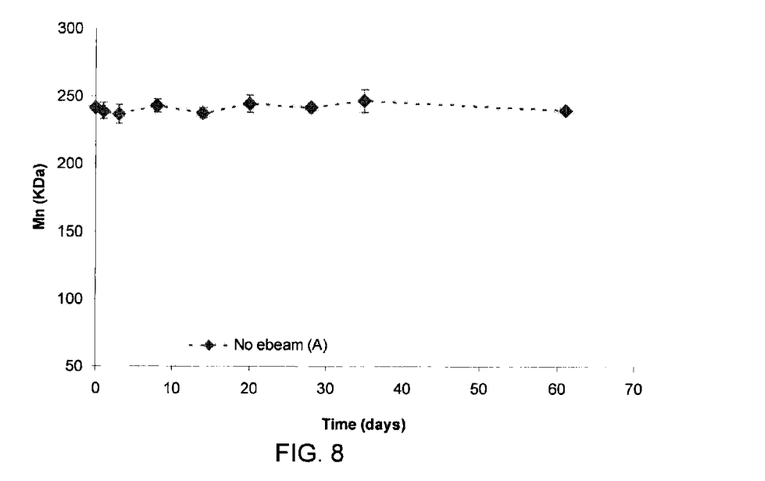
FIG. 8 depicts the Mn versus time of a PLLA scaffolding that is not irradiated with E-beam radiation.

Table 1 is a summary of the studies on the effect of E-beam sterilization on PLLA scaffolding samples. The samples in study A were not sterilized to provide a basis for comparison of the effect of E-beam radiation on molecular weight. The samples in studies B-E were sterilized with E-beam radiation with a dose of 27.5 kGy. The sterilization and storage conditions are in Table 1 for each study. FIG. 8 depicts the Mn versus time of a PLLA scaffolding corresponding to study A. The Mn is fairly constant as expected.

TABLE 1

Summary of studies on the effect of E-beam radiation on PLLA scaffolding samples.

| Study | Sterilization conditions for samples | Storage conditions for samples |
|---|---|---|
| A | Non-sterile - no irradiation | $RT^1$ storage in sealed foil pouch in argon |
| B | Sterilize in foil pouch in argon | RT storage in sealed foil pouch in argon |
| C | Sterilize in foil pouch in 1% $O_2$ | RT storage in sealed foil pouch in argon |
| D | Sterilize in Tyvek ® pouch - exposed to air | RT storage in sealed Tyvek ® pouch in argon |
| E | Sterilize in foil pouch in argon | 1. Expose to samples to air for 24 hrs 2. Seal and repack units in foil pouch in argon |

[1]RT = Room Temperature
Data collection A-D: 0, 1, 3, 7, 14, 21, 28, 35, 56, (180) days
Data collection E: 3, 7, 14, 21, 28, 35, 56, (180) days FIG. 9 depicts the Mn versus time for the samples of studies B-E. For study B, the sterilization and storage in inert gas and the effect were discussed above. In study B, the scaffolding Mn increased from about 80 kDa post-sterilization to above 100 kDa after about 60 days.

The comparison between study A, FIG. 8, and study B, FIG. 9, reveals the dramatic effect that radiation has on the long term behavior of Mn. The profile of Mn for study C, which is sterilization and storage in a 1% oxygen gas, in FIG. 9 shows only a slight increase in Mn the first day or so with stable Mn after the increase. For study D, which is sterilization in air, the initial Mn is lower than for studies B and C and is stable throughout the range studied. For study E, the initial molecular weight is also lower than for studies B and C and is stable throughout the range studied. The molecular weight for study D is slightly higher than for study E. This presence of oxygen during the sterilization in study D may increase the radiation induced chain scission resulting in a lower Mn.

A preferred embodiment used in the above studies has the stent pattern described in U.S. application Ser. No. 12/447,758 (US 2010/0004735) to Yang & Jow, et al. Other examples of stent patterns suitable for PLLA are found in US 2008/0275537. The cross-section of the struts of the scaffold is 150×150 microns.

Above it was stated that the molecular weight and properties of a polymeric stent can be stabilized after sterilization by aging a stent at room temperature or a slightly higher temperature. However, the final molecular weight after stabilizing would be a high end value at the end of the stabilization period. The methods of the present invention discussed above involve quenching the free radicals during or after sterilization so that the molecular weight is stabilized at or close to the molecular weight at the end of radiation sterilization.

Further embodiments of the present invention include allowing the molecular weight to increase for a period of time after sterilization, followed by stopping the molecular weight change through exposure of the stent to oxygen to stabilize the polymer at a desired Mn. The stabilized Mn can be any value between the Mn immediately after sterilization to the high end value at the end of stabilization through room temperature stabilization discussed above.

The method can include radiation sterilizing a stent disposed in a package with an inert gas atmosphere. After a selected period of time, the stent can then be exposed to an oxygen-containing gas, preferably, a high content of oxygen content such as air. The oxygen content may be high enough to rapidly terminate or quench the free radicals to stop the increase in molecular weight at a desire valued of Mn. For example, the free radical concentration may decay to less than $5 \times 10^7$ Dl/mg in less than 2 days, 1 day, 12 hr, 5 hr, 1 hr. The oxygen content of the gas may be greater than 5%, 5 to 10%, greater than 10%, 10 to 20%, 20% to air concentration, or greater than air concentration.

The method can include selecting a desired final Mn of the polymer scaffolding of the stent. The Mn versus time relationship post-sterilization may be determined in an inert gas atmosphere, such as that shown in FIG. 3. The selected time required for the scaffolding polymer to reach selected Mn may be obtained from the relationship. A scaffolding with the selected Mn may then be obtained by exposing a scaffolding packaged in an inert atmosphere at the selected time post-radiation sterilization.

Figure 10:
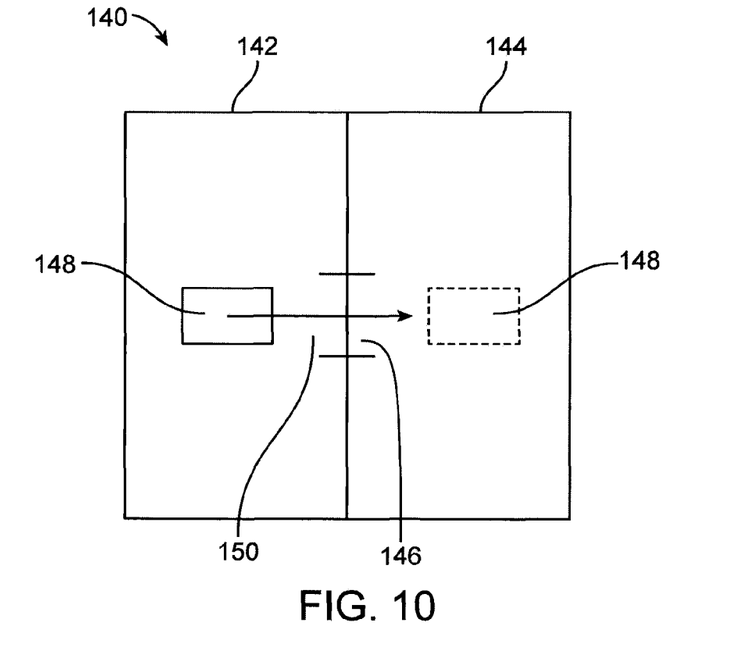
FIG. 10 depicts a schematic representation of a two-sided pouch having an aluminum side and a Tyvek® side, which has air within.

The above method may be achieved in a variety of ways. In one embodiment, a radiation sterilized stent may be placed in a pouch with two sides or enclosures. One side is made of a gas impermeable material such as aluminum and the other side is made of gas permeable material, Tyvek®. FIG. 10 depicts a schematic representation of a two-sided pouch 140 having a gas impermeable aluminum side 142 and a gas permeable Tyvek® side 144, which has air within. The two sides are sealed from one another and are connected by a movable sealer 146 that allows movement of a stent 148 from the aluminum side to the Tyvek® side without fluid communication between the sides. Before sterilization, stent 148 is placed in the aluminum side in an inert gas. The stent is sterilized and after a certain time post-sterilization, the sealer shifts the stent (shown in phantom) to the Tyvek® side, as shown by arrow 150, to terminate free radicals, and therefore to stop Mn change. After a selected stabilization time, the stent is shifted back to the aluminum side to the inert gas environment. The stent may then be stored in an inert gas environment by refilling with inert gas and resealing.

Alternatively, a package can have three compartments, a first compartment, a second compartment, and a third compartment. The second compartment that contains the stent is separated from the first compartment and the third compartment by a zipper or resealable tape. The zipper or tab can be positioned to allow or close off fluid communication between the first or third compartments. The first compartment and the second compartment are gas impermeable, for example, made of aluminum, and filled with inert gas. The third compartment is gas permeable, e.g., made of Tyvek®, and filled with air. During sterilization, the stent would remain in the second compartment and is sealed off from both the first and third compartments. After sterilization, the zipper or tab between the second and the third compartment is opened, exposing stent to air. After a certain time, the same zipper or tab is closed, and then the zipper or tab between the first and the second compartment is opened, exposing the stent to the inert gas environment again.

Figure 11:
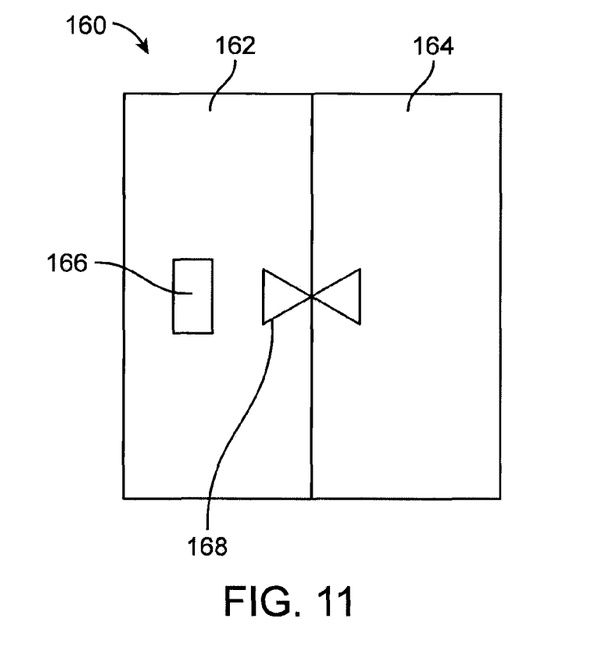
FIG. 11 depicts a schematic representation of a pouch with a first aluminum side and a second aluminum side.

In another embodiment, both sides of a pouch may be made from gas impermeable material such as aluminum. FIG. 11 depicts a schematic representation of a pouch 160 with two gas impermeable sides, a first aluminum side 162 and a second aluminum side 164. Prior to and during sterilization the first side 162 is filled with inert gas, while the second side 164 is filled with a mixture of an inert gas and oxygen. Prior to and during sterilization, a stent 166 is disposed in the first side 162 and the two sides are not fluidly connected. A selected period of time after sterilization when the Mn of the scaffolding reaches a selected Mn, the mixture of inert gas and oxygen may be used to terminate free radical recombination. For example, the mixture may have at least 1% oxygen, 1-5% oxygen, 5-15% oxygen, 15-20% oxygen, or is air. The two sides may be connected by a valve 168 that allows the two sides to be fluidly connected when the valve is open and sealed from one another when the valve is closed. During sterilization and a selected period time after sterilization valve 168 may be closed. After the selected period of time, valve 168 may be opened to allow the exposure of the stent to the inert gas and oxygen mixture to terminate the free radicals and stabilize the molecular weight at the selected Mn. After the molecular weight is stabilized valve 168 may be closed and the gas in the first side 162 may be replaced with an inert gas atmosphere.

For the purposes of the present invention, the following terms and definitions apply:

The Tyvek® packaging herein refers to Tyvek® medical packaging from Dupont of Wilmington, Del. such as DuPont™ Tyvek® 1073B.

The term "molecular weight" can refer to one or more definitions of molecular weight. "Molecular weight" can refer to the molecular weight of individual segments, blocks, or polymer chains. "Molecular weight" can also refer to weight average molecular weight or number average molecular weight of types of segments, blocks, or polymer chains. The number average molecular weight (Mn) is the common, mean, average of the molecular weights of the individual segments, blocks, or polymer chains. Molecular weight is typical expressed in grams/mole which is referred to as "Daltons." It is determined by measuring the molecular weight of N polymer molecules, summing the weights, and dividing by N:

$$\overline{M}_n = \frac{\sum_i N_i M_i}{\sum_i N_i}$$

where Ni is the number of polymer molecules with molecular weight Mi. The weight average molecular weight is given by $$\overline{M}_w = \frac{\sum_i N_i M_i^2}{\sum_i N_i M_i}$$

where Ni is the number of molecules of molecular weight Mi Unless otherwise specified, "molecular weight" will refer to number average molecular weight (Mn).

"Semi-crystalline polymer" refers to a polymer that has or can have regions of crystalline molecular structure and amorphous regions. The crystalline regions may be referred to as crystallites or spherulites which can be dispersed or embedded within amorphous regions.

The "glass transition temperature," Tg, is the temperature at which the amorphous domains of a polymer change from a brittle vitreous state to a solid deformable or ductile state at atmospheric pressure. In other words, the Tg corresponds to the temperature where the onset of segmental motion in the chains of the polymer occurs. When an amorphous or semi-crystalline polymer is exposed to an increasing temperature, the coefficient of expansion and the heat capacity of the polymer both increase as the temperature is raised, indicating increased molecular motion. As the temperature is increased, the heat capacity increases. The increasing heat capacity corresponds to an increase in heat dissipation through movement. Tg of a given polymer can be dependent on the heating rate and can be influenced by the thermal history of the polymer as well as its degree of crystallinity. Furthermore, the chemical structure of the polymer heavily influences the glass transition by affecting mobility.

The Tg can be determined as the approximate midpoint of a temperature range over which the glass transition takes place. [ASTM D883-90]. The most frequently used definition of Tg uses the energy release on heating in differential scanning calorimetry (DSC). As used herein, the Tg refers to a glass transition temperature as measured by differential scanning calorimetry (DSC) at a 20° C./min heating rate.

"Stress" refers to force per unit area, as in the force acting through a small area within a plane. Stress can be divided into components, normal and parallel to the plane, called normal stress and shear stress, respectively. Tensile stress, for example, is a normal component of stress applied that leads to expansion (increase in length). In addition, compressive stress is a normal component of stress applied to materials resulting in their compaction (decrease in length). Stress may result in deformation of a material, which refers to a change in length. "Expansion" or "compression" may be defined as the increase or decrease in length of a sample of material when the sample is subjected to stress.

"Strain" refers to the amount of expansion or compression that occurs in a material at a given stress or load. Strain may be expressed as a fraction or percentage of the original length, i.e., the change in length divided by the original length. Strain, therefore, is positive for expansion and negative for compression.

"Strength" refers to the maximum stress along an axis which a material will withstand prior to fracture. The ultimate strength is calculated from the maximum load applied during the test divided by the original cross-sectional area.

"Modulus" may be defined as the ratio of a component of stress or force per unit area applied to a material divided by the strain along an axis of applied force that results from the applied force. The modulus typically is the initial slope of a stress—strain curve at low strain in the linear region. For example, a material has both a tensile and a compressive modulus.

The tensile stress on a material may be increased until it reaches a "tensile strength" which refers to the maximum tensile stress which a material will withstand prior to fracture. The ultimate tensile strength is calculated from the maximum load applied during a test divided by the original cross-sectional area. Similarly, "compressive strength" is the capacity of a material to withstand axially directed pushing forces. When the limit of compressive strength is reached, a material is crushed.

"Toughness" is the amount of energy absorbed prior to fracture, or equivalently, the amount of work required to fracture a material. One measure of toughness is the area under a stress-strain curve from zero strain to the strain at fracture. The units of toughness in this case are in energy per unit volume of material. See, e.g., L. H. Van Vlack, "Elements of Materials Science and Engineering," pp. 270-271, Addison-Wesley (Reading, Pa., 1989).

The underlying structure or substrate of an implantable medical device, such as a stent can be completely or at least in part made from a biodegradable polymer or combination of biodegradable polymers, a biostable polymer or combination of biostable polymers, or a combination of biodegradable and biostable polymers. Additionally, a polymer-based coating for a surface of a device can be a biodegradable polymer or combination of biodegradable polymers, a biostable polymer or combination of biostable polymers, or a combination of biodegradable and biostable polymers.

It is understood that after the process of degradation, erosion, absorption, and/or resorption has been completed, no part of the stent will remain or in the case of coating applications on a biostable scaffolding, no polymer will remain on the device. In some embodiments, very negligible traces or residue may be left behind. For stents made from a biodegradable polymer, the stent is intended to remain in the body for a duration of time until its intended function of, for example, maintaining vascular patency and/or drug delivery is accomplished.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method of making a stent, comprising:
providing a package having an inner gas permeable layer and an outer gas impermeable layer, wherein the inner layer and the outer layer have an inert gas environment within and the inner layer and outer layer are sealed, wherein a polymer scaffolding is disposed within the inner layer;
exposing the scaffolding to E-beam radiation for sterilization;
allowing fluid communication between ambient air and the outer layer to expose the scaffolding to air for a period of time;
after the period of time, removing air from and sealing the gas impermeable package; and
storing the scaffolding in an inert gas environment.

2. A method of making a stent, comprising:
providing a package having a first side that is impermeable and a second side that is gas permeable,
wherein the first side has an inert gas environment within and the second side has ambient air,
wherein a polymeric scaffolding is disposed within the first side,
where the sides are connected by a movable sealer that allows movement of the scaffolding from the first side to the second side without fluid communication between the sides;
exposing the scaffolding to E-beam radiation for sterilization;
after a period of time after sterilization, shifting the scaffolding with the movable sealer to the second side to expose the stent to air; and
after a selected stabilization time, shifting the scaffolding to the first side to the inert gas environment; and
resealing the first side with inert gas.

3. A method of making a stent, comprising:
providing a package having a first side and a second side that are both gas impermeable,
wherein the first side has an inert gas environment and the second side has a mixture of an inert gas and oxygen,
wherein a polymeric scaffolding is disposed within the first side,
wherein the sides are connected by a valve that allows fluid communication between the first side to the second side when the valve is open;
exposing the scaffolding to E-beam radiation for sterilization;
after a period of time after sterilization, opening the valve to allow fluid communication between the first side and the second side to expose the scaffolding to oxygen and terminate free radicals in the scaffolding; and
after a selected stabilization time, closing the valve and replacing the inert gas and mixture in the first side with an inert gas environment.

* * * * *